United States Patent [19]

Ray et al.

[11] Patent Number: 4,931,043
[45] Date of Patent: Jun. 5, 1990

[54] RATCHET CONNECTOR FOR HYPODERMIC SYRINGE PISTONS

[75] Inventors: Jefferson L. Ray, McPherson; Michael E. Cooper, Meridian Township, McPherson County, both of Kans.

[73] Assignee: Sterling Drug Inc., New York, N.Y.

[21] Appl. No.: 229,394

[22] Filed: Aug. 8, 1988

[51] Int. Cl.⁵ .............................................. A61M 5/00
[52] U.S. Cl. .................................... 604/228; 604/218
[58] Field of Search ............... 604/228, 233, 229, 225, 604/224, 221, 220, 219, 218, 210, 209, 208, 193, 155, 154, 152, 151, 121; 403/287, 292, 296, 298, 299

[56] References Cited

U.S. PATENT DOCUMENTS

| | | |
|---|---|---|
| 1,395,592 | 11/1921 | Odom . |
| 2,524,367 | 10/1950 | Smith . |
| 3,224,445 | 12/1965 | Melott . |
| 3,253,625 | 5/1966 | Oestereicher . |
| 3,259,130 | 7/1966 | Krauthamer . |
| 3,273,443 | 9/1966 | Rubin . |
| 3,555,491 | 1/1971 | Moss . |
| 3,584,667 | 6/1971 | Reiland . |
| 4,125,051 | 11/1978 | Herkes et al. . |
| 4,293,256 | 10/1981 | Pamer . |
| 4,759,750 | 7/1988 | DeVries et al. ...................... 604/121 |

FOREIGN PATENT DOCUMENTS 0128039 12/1984 European Pat. Off. ............ 403/287

Primary Examiner—C. Fred Rosenbaum
Assistant Examiner—Adam J. Cermak
Attorney, Agent, or Firm—William G. Webb; Paul E. Dupont

[57] ABSTRACT

A connector for attachment of a plunger to a rubber piston in hypodermic syringe cartridge ampoules comprises a pin having a shank portion with a contiguous screw-threaded post portion and a ratchet head portion sized to rotatably fit within a cavity in said piston which thus prevents overtightening the plunger to the piston thereby obviating jamming of the piston in the bore of the cartridge.

8 Claims, 2 Drawing Sheets

RATCHET CONNECTOR FOR HYPODERMIC SYRINGE PISTONS

BACKGROUND OF THE INVENTION

This invention relates to the field of disposable ampoules for use in hypodermic syringes. It particularly relates to a novel means of attachment of a plunger to the slidable piston in such ampoules via a screw-threaded attachment.

INFORMATION DISCLOSURE STATEMENT

The general concept of the use of a ratchet, or ratchet in combination with a pawl, to control rotary motion of various mechanical devices is well known in the prior art.

For example Odom U.S. Pat. No. 1,395,592 discloses an overwinding preventer for use in connection with the winding shaft of a spring motor. The preventer comprises a spring member M of general V-shape pivoted about its apex in which one arm portion constantly bears against a generally cylindrical block 8 and the end of the other arm bears against one of four bolts. The periphery of the block has recesses 16 with shoulders (a) for engagement of the first arm of spring M. The spring and block with the recesses and shoulders thus function as a pawl and ratchet which allow the block to turn in one direction, i.e. away from the end of the V-shaped spring, but not in the reverse direction.

Rubin U.S. Pat. No. 3,273,443 discloses a limited torque nut and bolt adapted to ensure that the nut cannot be overtightened. The nut consists of a base portion 75, with a cylindrical portion 76 which is bored and threaded internally for engagement with a bolt, and a rotary member 82 with a hexagon head and a depending cylindrical portion 84. The base portion and the rotary member each have ratchet teeth 81 and 85, respectively, adapted for engagement with one another. The rotary member has a rolled collar 80 which holds a spring washer 86 in engagement with the upper face of the rotary member. When the rotary member is turned down over the base member, the spring washer controls the amount of pressure exerted by ratchet teeth 85 on mating teeth 81 causing the teeth to slip past one another once a certain maximum force is exerted between the teeth.

Moss U.S. Pat. No. 3,555,491 discloses a torque limiting screw type connector for joining polarizing pins for parts of a separable electrical connector. The invention relies on use of mating interengaged ratchets with limitation in the torque determined by tension provided by a compression spring 89 against one portion of two ratchet units consisting of "clutch" plates 64 with ratchet teeth 69 and nut 54 with ratchet teeth 60.

Other means for controlling or affecting the degree of tightening of screw-threaded engagements are exemplified by the following:

Oestereicher U.S. Pat. No. 3,253,625 discloses a driving bit for non-removable screw fasteners which positively engages the screw when the bit is rotated in the driving direction but disengages when rotated in the opposite direction.

Reiland U.S Pat. No. 3,584,667 discloses means for transmitting torque from a driving to a driven unit by means of interengaged hex-lobular configured mating faces on each of the driving and the driven units. The configuration allows the units to slip over one another when excessive torque is applied.

Herkes et al. U.S. Pat. No. 4,125,051 discloses screw threaded fasteners which have a head of such design that a driving tool will positively interengage the head in the driving direction but will disengage when rotated in the opposite direction. The generally flat head of the fastener has a series of radial ribs 24 with sloped camming surfaces 28 and driving surfaces 26 essentially perpendicular to the flat head of the fasteners. The driving tool has an appropriately configured driving face to mate with the driving surfaces on the fastener.

Pamer U.S. Pat. No. 4,293,256 discloses a screw-type fastener with a load indicating feature to provide visual indication when a predetermined torque has been applied to the fastener. The load indicating feature comprises undulations or waves around the periphery of the load transmitting head of the screw which flatten out when sufficient torque is applied to the fastener.

Various means of attaching a plunger to a rubber piston in hypodermic syringe ampoules are illustrated by Smith U.S. Pat. No. 2,524,367 which discloses a syringe having a blade-like head 55 on the distal end of the plunger which must be aligned with a slot 70 in the proximal face of the piston. The slot opens into recesses 71 inside the piston so that, when the blade enters the slot and is given a one quarter turn, the blade is locked into the recess end of the piston.

Melott U.S. Pat. No. 3,224,445 discloses a syringe having a barbed spear point engagement means on the plunger end for embedding in the piston.

Krauthamer U.S. Pat. No. 3,259,130 discloses a similar barbed spear type of engagement means on the plunger end for embedding in the piston.

BRIEF DESCRIPTION OF THE INVENTION

The present invention relates to a connector for attaching a plunger to a slidable flexible piston in cartridge-type ampoules via a screw threaded attachment which comprises a pin for coupling said plunger to said piston, said pin comprising a cylindrical shank portion, a ratchet head portion on one end thereof of larger overall diameter than said shank portion and a screw-threaded post portion on the other end wherein said ratchet head portion has a plurality of ratchet teeth around its periphery.

In a further aspect, the invention relates to a device for use in a hypodermic injection system which comprises the connector in combination with a flexible rubber piston.

In a still further aspect, the invention relates to a device for use in a hypodermic injection system which comprises the connector in combination with a flexible rubber piston and a cartridge ampoule.

DETAILED DESCRIPTION OF THE INVENTION

Figure 1:
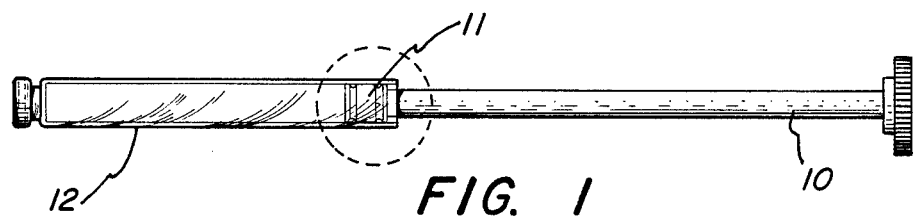
FIG. 1 is a plan view of a cartridge ampoule and associated plunger.
Figure 2:
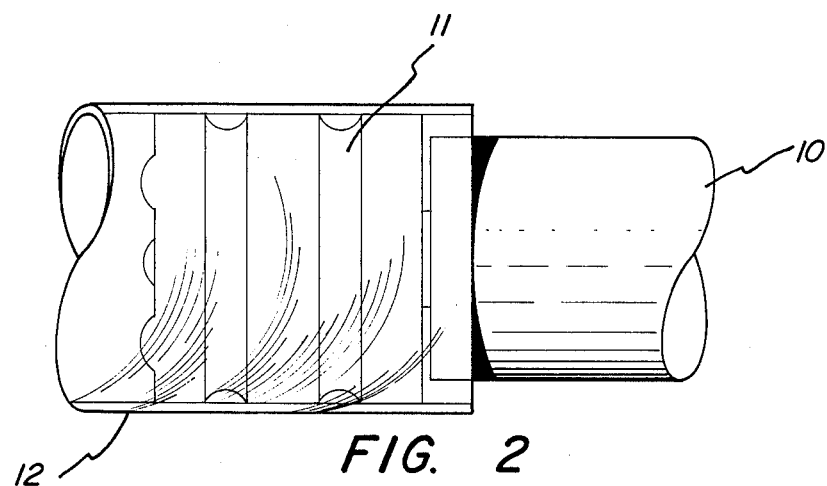
FIG. 2 is an enlarged fragmentary plan view of the portion of FIG. 1 shown within the dotted circle of FIG. 1.

With reference to FIGS. 1 and 2, the novel connector of the present invention serves to attach a plunger 10 to a rubber piston 11 which is slidable within the bore of a glass ampoule or cartridge 12 of the type conventionally used in hypodermic injection cartridge holders such as described, for example, in U.S. Pat. No. 4,585,445. In such conventional combinations of cartridge and plunger, the plunger is equipped with a screw threaded hole in the distal end of the plunger shaft and is attached to the piston via a screw-threaded post which is securely embedded within the rubber piston. However, such conventional means of connecting the plunger to the piston suffers the disadvantage that even slight overtightening of the plunger to the piston causes significant distortion of the flexible rubber piston with the result that the piston tends to expand radially thus causing the piston to jam in the syringe barrel. The connector of the present invention overcomes that disadvantage.

Figure 3:
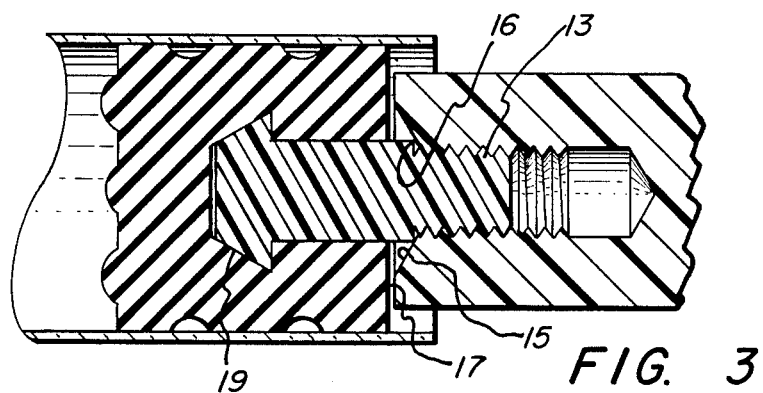
FIG. 3 is a cross-sectional view of the piston, connector and plunger shown in FIG. 2.

With reference to FIG. 3, the connector of the invention, 13, has a cylindrical central shank portion, a screw threaded portion on its proximal end for attachment to the plunger and a ratchet head portion on the distal end with a bevelled forward face 19. The ratchet head portion and a substantial part of the shank portion are held within a cavity in the rubber piston which is shaped to accommodate the ratchet head and the shank portions of the connector.

Figure 4B:
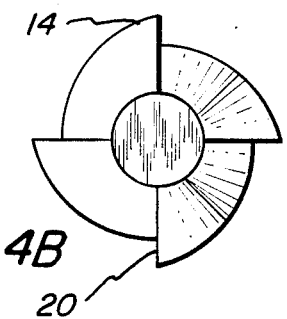
FIGS. 4A and 4B are plan and end views, respectively, of the ratchet head configuration of one embodiment of the connector of the invention.
Figure 4A:
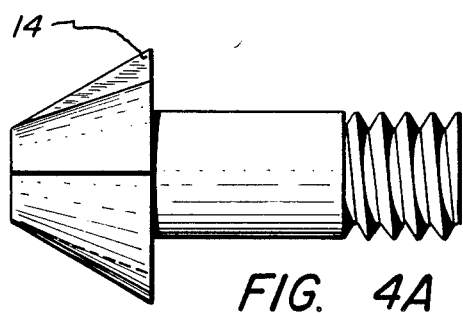

In the embodiment depicted in FIGS. 4A/4B, the ratchet head portion of the connector has a plurality of ratchet teeth 14, with gripping edges 20, which allow the connector to turn within the cavity when the head is rotated in the direction such that the gripping edges are at the trailing edge of each ratchet teeth. However the relative sizes of the cavity and shank/ratchet head portions of the connector are such that there is a sufficient amount of frictional resistance to turning that the plunger can be screwed onto the threaded post in the piston.

In order to ensure that the connector can turn within the cavity when the plunger is fully engaged with the connector, it is essential that a slight gap 17, shown in FIG. 3, be left between the proximal face of the piston and the distal face of the plunger. This can be achieved by proper sizing of the length of the threaded portion of the connector and the depth of the threaded hole in the end of the plunger. Another means of accomplishing the same objective is shown in FIG. 3. As there depicted, the plunger has a bevelled portion 15 which seats on a shoulder 16 of the connector shank, and the length of the shank portion is so dimensioned relative to the depth of the threaded hole in the end of the plunger that the necessary gap is left between the proximal face of the piston and the distal face of the plunger.

When the plunger is turned in the opposite direction to detach it from the connector, the ratchet teeth will engage the walls of the cavity to thus prevent reverse rotation of the connector within the cavity and to permit removal of the plunger from the cartridge and removal of the cartridge from the syringe holder for disposal. The wall of the cavity thus acts as an essentially continuous pawl to prevent counter rotation of the ratchet head within the cavity.

Figure 6:
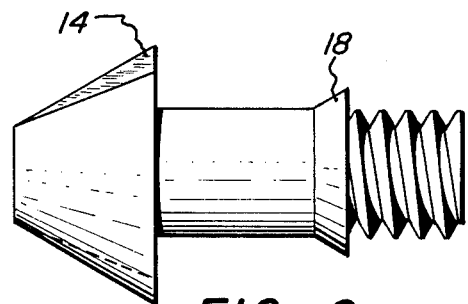
FIG. 6 is a plan view of a modified shank configuration of the connector of the invention.

In the connector configuration depicted in FIG. 6 the shank is provided with a flared portion 18 on the end of the shank adjacent the threaded portion which provides a broadened shoulder, similar to shoulder 16, which abuts the bevelled portion 15 on the distal end of the plunger when the two units are fully engaged with one another thereby preventing interengagement of the proximal face of the piston and the distal face of the plunger and consequent overtightening of the plunger to the piston.

Figure 5B:
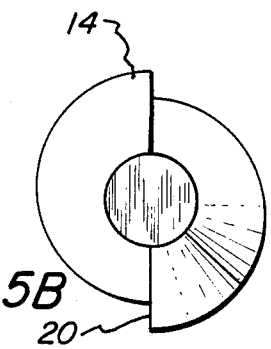
FIGS. 5A and 5B are plan and end views, respectively, of the ratchet head configuration of an alternative embodiment of the connector of the invention.
Figure 5A:
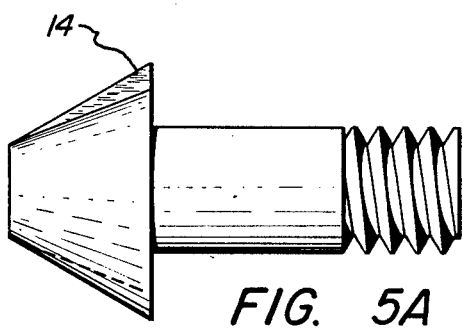

FIGS. 5A and 5B depict an alternative ratchet head configuration having only two ratchet teeth instead of four as depicted in FIGS. 4A and 4B. The number of ratchet teeth on the connector head is thus not a critical aspect of the connector of the invention, and any number of teeth that will serve the purpose of the invention can be used.

It will be seen that the threads on the screw threaded post and the mating threads in the end of the plunger are depicted in the drawings hereof as being right-handed, i.e. the plunger is attached to the threaded post by clockwise rotation, which is the conventional means of attachment in ampoules of the type here generally described. However it will be appreciated that the inventive concept will operate equally well with left-hand threaded posts and plungers, the set of the ratchet teeth in the head being reversed as well, and such alternate means of attachment of the two elements to one another is contemplated by the invention.

Because of the flexibility of the rubber pistons used with the connectors and the bevelled face on the head of the latter, the connectors of the invention are readily assembled with the pistons by forcing the ratchet head portion of the connector into the cavity in the piston until the ratchet head becomes trapped within the cavity.

The connectors are fabricated either by machining from an appropriate metal, such as stainless steel or brass, or from plastic. Alternatively they may be molded from a suitable plastic material. Preferred materials for use in fabricating the connectors are chrome-plated brass or a plastic material, for example Delrin ®.

Having thus described the invention and the advantages thereof, it is considered that the invention is to be broadly construed and limited only by the character of the following claims.

We claim:

1. A device for use in a hypodermic injection system which comprises in combination a slidable piston with a hollow recess therein and connector means for attaching a plunger to said piston, said connector means comprising a pin, said pin being disposed within said hollow recess of said piston, said pin having a cylindrical shank portion, a ratchet head portion on one end thereof of larger overall diameter than said shank portion and a screw-threaded post portion on the other end thereof wherein said ratchet head portion has a plurality of ratchet teeth arranged around its periphery.

2. A device according to claim 1 wherein the shank portion of said pin has a shoulder adjacent said screw-threaded post portion.

3. A device according to claim 2 wherein said shoulder comprises a flared portion on the end of said shank portion adjacent said screw-threaded post portion.

4. A device according to claim 1 wherein the ratchet head portion of said pin is equipped with four ratchet teeth.

5. A device for use in a hypodermic injection system which comprises in combination a hollow cylindrical cartridge ampoule, a flexible piston slidable in the bore thereof and connector means for attaching a plunger to said slidable piston, said piston having a hollow recess therein, said connector means comprising a pin being disposed within said hollow recess of said piston and having a cylindrical shank portion, a ratchet head portion on one end thereof of larger overall diameter than said shank portion and a screw-threaded post portion on the other end thereof wherein said ratchet head portion has a plurality of ratchet teeth arranged around its periphery.

6. A device according to claim 5 wherein the shank portion of said pin has a shoulder adjacent said screw-threaded post portion.

7. A device according to claim 6 wherein said shoulder comprises a flared portion on the end of said shank portion adjacent said screw-threaded post portion.

8. A device according to claim 5 wherein the head portion of said pin is equipped with four ratchet teeth.

* * * * *